(12) United States Patent
Gauvry et al.

(10) Patent No.: US 8,168,681 B2
(45) Date of Patent: May 1, 2012

(54) AMIDOACETONITRILE COMPOUNDS AND PESTICIDAL COMPOSITION THEREOF

(75) Inventors: Noëlle Gauvry, Kembs (FR); Thomas Goebel, Lörrach (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/130,807

(22) PCT Filed: Dec. 2, 2009

(86) PCT No.: PCT/EP2009/066254
§ 371 (c)(1),
(2), (4) Date: May 24, 2011

(87) PCT Pub. No.: WO2010/063767
PCT Pub. Date: Jun. 10, 2010

(65) Prior Publication Data
US 2011/0230563 A1    Sep. 22, 2011

(30) Foreign Application Priority Data

Dec. 3, 2008    (EP) .................................... 08170579

(51) Int. Cl.
*A01N 37/34* (2006.01)
*C07C 255/42* (2006.01)
(52) U.S. Cl. ........................................ 514/618; 558/392
(58) Field of Classification Search ................. 514/618; 558/392
See application file for complete search history.

(56) References Cited

FOREIGN PATENT DOCUMENTS

| WO | WO 03/097585 A2 | 11/2003 |
|---|---|---|
| WO | WO 03/104187 A1 | 12/2003 |
| WO | WO 2005/044784 A1 | 5/2005 |
| WO | WO 2005/058802 A1 | 6/2005 |
| WO | WO 2007/017088 A1 | 2/2007 |
| WO | WO 2008/096231 A1 | 8/2008 |

OTHER PUBLICATIONS

ISR, 2010.
Written Opinion, 2011.

*Primary Examiner* — Kamal Saeed
*Assistant Examiner* — Kristin Bianchi
(74) *Attorney, Agent, or Firm* — Ann R. Pokalsky, Esq; Dilworth & Barrese, LLP

(57) ABSTRACT

Novel amidoacetonitrile compounds are disclosed. The compounds have pesticidal properties and are suitable for controlling endoparasites on warm-blooded animals.

15 Claims, No Drawings

AMIDOACETONITRILE COMPOUNDS AND PESTICIDAL COMPOSITION THEREOF

CROSS-REFERENCE TO RELATED APPLICATIONS

This application claims priority to PCT Application Number PCT/EP2009/066254, filed Dec. 2, 2009, which claims priority to EP Application Number 08170579.0, filed Dec. 3, 2008.

The present invention relates to new amidoacetonitrile compounds of formula

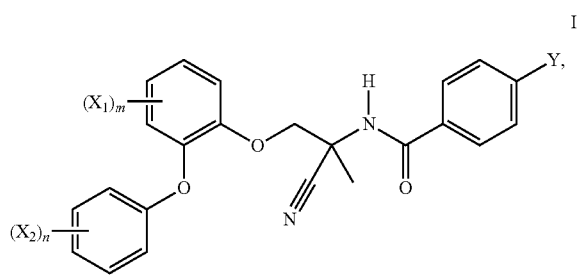

wherein
$X_1$ signifies cyano or halogen, whereby if m is greater than 1, the meanings of $X_1$ may be identical or different;
$X_2$ signifies halogen, cyano, $C_1C_6$-alkyl, $C_1$-$C_6$-haloalkyl, $C_1$-$C_6$-alkoxy, $C_1$-$C_6$-haloalkoxy, $C_1$-$C_6$-haloalkylthio or $SF_5$,
whereby if n is greater than 1, the meanings of $X_2$ may be identical or different;
Y is $C_1$-C2-haloalkyl, SR, S(O)R, $S(O_2)R$ or $SF_5$,
R is $C_1$-$C_6$-alkyl or $C_1$-$C_6$-haloalkyl,
m signifies 1, 2, 3 or 4; and
n is 1, 2, 3, 4 or 5;
subject to the proviso, that Y is $SF_5$ if $X_1$ is cyano,
each respectively in free form or in salt form, their preparation and usage in the control of endo- and ectoparasites, especially helminths, in and on warm-blooded animals, especially productive livestock and domestic animals, as well as on plants, furthermore pesticides which contain at least one of these compounds.

Substituted amidoacetonitrile compounds having pesticidal activity are described, for example, in WO 2003/104187, WO 2005/58802 or WO 2008/96231. However, the active ingredients specifically disclosed therein cannot always fulfill the requirements regarding potency and activity spectrum. There is therefore a need for active ingredients with improved pesticidal properties. It has now been found that the amidoacetonitrile compounds of formula I have excellent pesticidal properties, especially against endo- and ecto-parasites in and on warm-blooded animals and plants.

Alkyl—as a group per se and as structural element of other groups and compounds, for example haloalkyl,—is, in each case with due consideration of the specific number of carbon atoms in the group or compound in question, either straight-chained, i.e. methyl, ethyl, propyl, butyl, pentyl or hexyl, or branched, e.g. isopropyl, isobutyl, sec-butyl, tert-butyl, isopentyl, neopentyl or isohexyl. Alkyl is preferably methyl ethyl or n- or iso-propyl, in particular methyl.

Halogen—as a group per se and as structural element of other groups and compounds such as haloalkyl, or haloalkoxy,—is, for example, fluorine, chlorine, bromine or iodine, especially fluorine, chlorine or bromine, in particular fluorine or chlorine.

Halogen-substituted carbon-containing groups and compounds, such as haloalkyl, haloalkoxy or haloalkylthio, may be partially halogenated or perhalogenated, whereby in the case of multiple halogenation, the halogen substituents may be identical or different. Examples of halogen-alkyl—as a group per se and as structural element of other groups and compounds such as haloalkoxy or haloalkylthio,—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl2$, $CF_2CHF_2$, $CF_2CFCl_2$, $CF_2CHBr_2$, $CF_2CHClF$, $CF_2CHBrF$ or $CClFCH-ClF$; propyl or isopropyl, mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; butyl or one of its isomers, mono- to nonasubstituted by fluorine, chlorine and/or bromine, such as $CF(CF_3)CHFCF_3$ or $CH2(CF_2)_2CF_3$; pentyl or one of its isomers substituted once to eleven times by fluorine, chlorine and/or bromine, such as $CF(CF_3)(CHF)_2CF_3$ or $CH_2(CF_2)_3CF_3$; and hexyl or one of its isomers substituted once to thirteen times by fluorine, chlorine and/or bromine, such as $(CH_2)_4CHBrCH_2Br$, $CF_2(CHF)_4CF_3$, $CH_2(CF_2)CF_3$ or $C(CF_3)_2(CHF)_2CF_3$. Haloalkyl is most preferably trifluoromethyl ($CF_3$).

Alkoxy groups preferably have a chain length of 1 to 6 carbon atoms. Alkoxy is for example methoxy, ethoxy, propoxy, isopropoxy, n-butoxy, isobutoxy, sec.-butoxy and tert.-butoxy, as well as the isomers pentyloxy and hexyloxy; preferably methoxy and ethoxy. Haloalkoxy groups preferably have a chain length of 1 to 6 carbon atoms. Haloalkoxy is e.g. fluoromethoxy, difluoromethoxy, trifluoromethoxy, 2,2,2-trifluoroethoxy, 1,1,2,2-tetrafluoroethoxy, 2-fluoroethoxy, 2-chloroethoxy; 2,2-difluoroethoxy and 2,2,2-trichloroethoxy; preferably difluoromethoxy, 2-chloroethoxy and trifluoromethoxy, in particular trifluoromethoxy.

The variable m preferably is an integer of 1 or 2, in particular 1. If m is 1, the radical $X_1$ is positioned, for example, in the 4- or 5-position, preferably in the 5-position, of the 2-[$(X_2)_n$-phenoxy]-phenoxy ring.

$X_1$ is preferably cyano, fluorine, chlorine or bromine. In one embodiment of the invention $X_1$ is cyano. In another embodiment of the invention $X_1$ is halogen, preferably fluorine, chlorine or bromine, more preferably chlorine or bromine, and in particular chlorine.

The variable n is preferably an integer of 1, 2 or 3, more preferably 2 or 3, and especially 2. If n is 2, the two $X_2$ radicals are positioned preferably in the 2- and 4-position of the phenoxy ring.

Each $X_2$ independently is preferably halogen, cyano, $C_1$-$C_2$-haloalkyl or $C_1$-$C_2$-haloalkoxy, preferably halogen, $CF_3$ or $OCF_3$, and even more preferably fluorine, chlorine, bromine, $CF_3$ or $OCF_3$, and in particular fluorine, chlorine bromine or $OCF_3$.

The variable R is preferably $C_1$-$C_2$-alkyl or $C_1$-$C_2$-haloalkyl and in particular methyl, ethyl or $CF_3$.

According to one preferred embodiment of the invention Y is $SF_5$. According to another preferred embodiment of the invention Y is SR or $S(O_2)R$, wherein for R the above given meanings and preferences apply; according to this embodiment Y is most preferably $SCF_3$, $S(O_2)CF_3$ or $S(O_2)CH_3$. According to a further preferred embodiment of the invention Y is $CF_3$.

The compounds of the present invention have an asymmetric carbon atom in the 1-position labelled with (1*) in the formula I' below

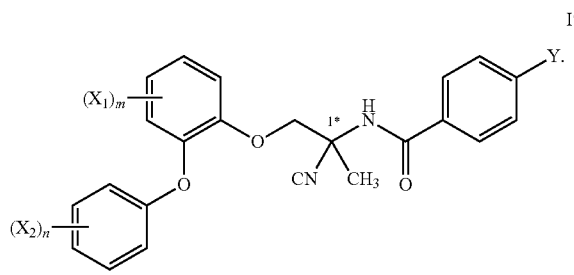

Accordingly, the compounds of formula I may exist as optical isomers. The present invention includes individual enantiomers of the compounds of formula I and mixtures thereof, including racemates.

The compounds of formula I may exist as geometric isomers. The present invention includes such compounds in the cis (Z-) or trans (E-) configuration, as well as mixtures of these geometric isomers.

The compounds of formula I may exist in more than one tautomeric form. The present invention encompasses all tautomers, as well as mixtures thereof.

Certain compounds of formula I may be able to form salts with acids or bases. The present invention includes said compounds of formula I in form of a salt to the extent that they are pharmaceutically or veterinarily acceptable.

The compounds of formula I and their salts may exist in unsolvated or solvated forms. The term solvate herein describes a molecular complex comprising the compound of formula I and one or more pharmaceutically or veterinarily acceptable solvents, for example ethanol or water. In case of water. The term "hydrate" is used.

Preferred embodiments within the scope of the invention are:
(0) A compound of formula I, wherein $X_1$ signifies cyano or halogen, whereby if m is greater than 1, the meanings of $X_1$ may be identical or different; $X_2$ signifies halogen, cyano, $C_1$-$C_6$-alkyl, $C_1$-$C_6$-haloalkyl, $C_1$-$C_6$-alkoxy or $C_1$-$C_6$-haloalkoxy, whereby if n is greater than 1, the meanings of $X_2$ may be identical or different; Y is $C_1$-$C_2$-haloalkyl, SR, S(O)R, S($O_2$)R or $SF_5$; R is $C_1$-$C_6$-alkyl or $C_1$-$C_6$-haloalkyl; m signifies 1, 2, 3 or 4; and n is 1, 2, 3, 4 or 5; subject to the proviso, that Y is $SF_5$ if $X_1$ is cyano.
(1) A compound of formula I, wherein m is 1; $X_1$ is cyano or halogen; n is 1, 2 or 3; each $X_2$ is independently of the other halogen, cyano, $C_1$-$C_2$-haloalkyl or $C_1$-$C_2$-haloalkoxy; Y is $SF_5$, $C_1$-$C_2$-haloalkyl, SR, S(O)R or S($O_2$)R; and R is $C_1$-$C_2$-alkyl or $C_1$-C2-haloalkyl, subject to the proviso that Y is $SF_5$ if $X_1$ is cyano.
(2) A compound of formula I, wherein Y is $SF_5$.
(3) A compound of formula I wherein Y is $C_1$-$C_2$-haloalkyl, SR, S(O)R or S($O_2$)R, and each $X_1$ independently of the other is halogen.
(4) A compound of formula I, wherein m is 1; $X_1$ is cyano or halogen; n is 1, 2 or 3; each $X_2$ is independently of the other halogen, cyano, $C_1$-$C_2$-haloalkyl or $C_1$-$C_2$-haloalkoxy and Y is $SF_5$.
(5) A compound of formula I, wherein m is 1; $X_1$ is cyano; n is 2 or 3; each $X_2$ is Independently of the other halogen, $CF_3$ or $OCF_3$, and Y is $SF_5$.
(6) A compound of formula I, wherein m is 1; $X_1$ is halogen, in particular chlorine, n is 2 or 3; each $X_2$ is independently of the other halogen, $CF_3$ or $OCF_3$, and Y is $SF_5$.
(7) A compound of formula I, wherein m is 1; $X_1$ is cyano or halogen, in particular cyano or chlorine, n is 2; each $X_2$ is independently of the other fluorine, chlorine or bromine, and Y is $SF_5$.
(8) A compound of formula I, wherein m is 1; $X_1$ is halogen; n is 1, 2 or 3; each $X_2$ is independently of the other halogen, cyano, $C_1$-$C_2$-haloalkyl or $C_1$-$C_2$-haloalkoxy; Y is $C_1$-$C_2$-haloalkyl, SR, S(O)R or S($O_2$)R; and R is $C_1$-$C_2$-alkyl or $C_1$-$C_2$-haloalkyl.
(9) A compound of formula I, wherein m is 1; $X_1$ is halogen; n is 1, 2 or 3; each $X_2$ is independently of the other halogen, $CF_3$ or $OCF_3$, and Y is $CF_3$, $SCF_3$, S($O_2$)$CF_3$ or S($O_2$)$CH_3$, in particular $SCF_3$, S($O_2$)$CF_3$ or S($O_2$)$CH_3$.
(10) A compound of formula

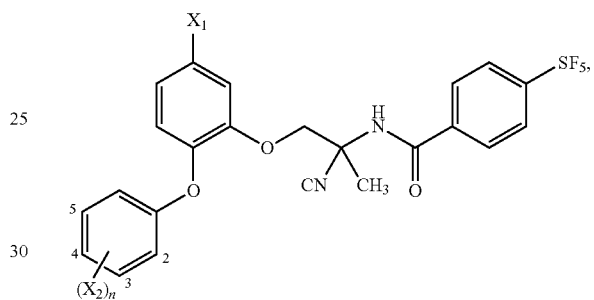

wherein for $X_1$, $X_2$ and n the above given meanings and preferences apply; more preferably a compound of the formula (Ia) above, wherein $X_1$ is cyano or halogen, in particular cyano, n is 1, 2 or 3, and each $X_2$ is independently of the other halogen, $CF_3$ or $OCF_3$; in particular a compound of the formula (Ia) above, wherein $X_1$ is cyano or chlorine, in particular cyano, n is 2, each $X_2$ is independently fluorine, chlorine or bromine, and the two radicals $X_2$ are positioned in the 2- and 4-position of the phenoxy ring.
(11) A compound of formula

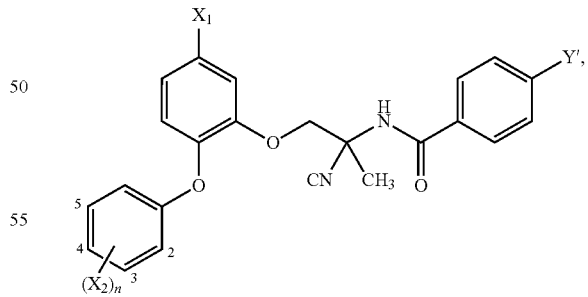

wherein Y' is $C_1$-$C_2$-haloalkyl, SR, S(O)R or S($O_2$)R, $X_1$ is halogen, and for $X_2$, n and R each the above given meanings and preferences apply; more preferably a compound of the formula (Ib) above, wherein Y' is $CF_3$, $SCF_3$, S($O_2$)$CF_3$ or S($O_2$)$CH_3$, $X_1$ is halogen, in particular chlorine, n is 2 or 3, in particular 2, each $X_2$ is independently fluorine, chlorine, bromine $CF_3$ or $OCF_3$, and if n is 2, the two radicals $X_2$ are positioned in the 2- and 4-position of the phenoxy ring.

Within the context of the invention, particular preference is given to the compounds of formula I listed below:

N-[1-cyano-1-methyl-2-(5-chloro-2-{2,4-dichlorophenoxy}-phenoxy)-ethyl]-4-pentafluorothio-benzamide,
N-[(1R)-1-cyano-1-methyl-2-(5-chloro-2-{2,4-dichlorophenoxy}-phenoxy)-ethyl]-4-pentafluorothio-benzamide,
N-[(1S)-1-cyano-1-methyl-2-(5-chloro-2-{2,4-dichlorophenoxy}-phenoxy)]-4-pentafluorothio-benzamide,
N-[1-cyano-1-methyl-2-(5-cyano-2-{2,4-dichlorophenoxy}-phenoxy)-ethyl]-4-pentafluorothio-benzamide,
N-[(1R)-1-cyano-1-methyl-2-(5-cyano-2-{2,4-dichlorophenoxy}-phenoxy)-ethyl]-4-pentafluorothio-benzamide,
N-[(1S)-1-cyano-1-methyl-2-(5-cyano-2-{2,4-dichlorophenoxy}-phenoxy)-ethyl]-4-pentafluorothio-benzamide,
N-[1-cyano-1-methyl-2-(5-cyano-2-{2-bromo-4-fluorophenoxy}-phenoxy)-ethyl]-4-pentafluorothio-benzamide,
N-[(1R)-1-cyano-1-methyl-2-(5-cyano-2-{2-bromo-4-fluorophenoxy}-phenoxy)-ethyl]-4-pentafluorothio-benzamide,
N-[(1S)-1-cyano-1-methyl-2-(5-cyano-2-{2-bromo-4-fluorophenoxy}-phenoxy)-ethyl]-4-pentafluorothio-benzamide,
N-[1-cyano-1-methyl-2-(5-cyano-2-{2-chloro-4-fluorophenoxy}-phenoxy)-ethyl]-4-pentafluorothio-benzamide,
N-[(1R)-1-cyano-1-methyl-2-(5-cyano-2-{2-chloro-4-fluorophenoxy}-phenoxy)-ethyl]-4-pentafluorothio-benzamide,
N-[(1S)-1-cyano-1-methyl-2-(5-cyano-2-{2-chloro-4-fluorophenoxy}-phenoxy)-ethyl]-4-pentafluorothio-benzamide,
N-[1-cyano-1-methyl-2-(5-cyano-2-{2-chloro-4-trifluorophenoxy}-phenoxy)-ethyl]-4-pentafluorothio-benzamide,
N-[(1R)-1-cyano-1-methyl-2-(5-cyano-2-{2-chloro-4-trifluorophenoxy}-phenoxy)-ethyl]-4-pentafluorothio-benzamide,
N-[(1S)-1-cyano-1-methyl-2-(5-cyano-2-{2-chloro-4-trifluorophenoxy}-phenoxy)-ethyl]-4-pentafluorothio-benzamide,
N-[1-cyano-1-methyl-2-(5-chloro-2-{2,4-dichlorophenoxy}-phenoxy)-ethyl]-4-trifluoromethylthio-benzamide,
N-[(1R)-1-cyano-1-methyl-2-(5-chloro-2-{(2,4-dichlorophenoxy}-phenoxy)-ethyl]-4-trifluoromethylthio-benzamide,
N-[(1S)-1-cyano-1-methyl-2-(5-chloro-2-{2,4-dichlorophenoxy}-phenoxy)-ethyl]-4-trifluoromethylthio-benzamide,
N-[1-cyano-1-methyl-2-(4-chloro-2-{2,4-dichlorophenoxy}-phenoxy)-ethyl]-4-trifluoromethylthio-benzamide,
N-[(1R)-1-cyano-1-methyl-2-(4-chloro-2-{(2,4-dichlorophenoxy}-phenoxy)-ethyl]-4-trifluoromethylthio-benzamide,
N-[(1S)-1-cyano-1-methyl-2-(4-chloro-2-{2,4-dichlorophenoxy}-phenoxy)-ethyl]-4-trifluoromethylthio-benzamide,
N-[1-cyano-1-methyl-2-(5-chloro-2-{2-bromo-3,5-difluorophenoxy}-phenoxy)-ethyl]-4-trifluoromethylthio-benzamide,
N-[(1R)-1-cyano-1-methyl-2-(5-chloro-2-{2-bromo-3,5-difluorophenoxy}-phenoxy)-ethyl]-4-trifluoromethylthio-benzamide,
N-[(1S)-1-cyano-1-methyl-2-(5-chloro-2-{2-bromo-3,5-difluorophenoxy}-phenoxy)-ethyl]-4-trifluoromethylthio-benzamide,
N-[1-cyano-1-methyl-2-(4-bromo-2-{2,4-dichlorophenoxy}-phenoxy)-ethyl]-4-trifluoromethylthio-benzamide,
N-[(1R)-1-cyano-1-methyl-2-(4-bromo-2-{(2,4-dichlorophenoxy}-phenoxy)-ethyl]-4-trifluoromethylthio-benzamide,
N-[(1S)-1-cyano-1-methyl-2-(4-bromo-2-{2,4-dichlorophenoxy}-phenoxy)-ethyl]-4-trifluoromethylthio-benzamide,
N-[1-cyano-1-methyl-2-(5-chloro-2-{2,4-dichlorophenoxy}-phenoxy)-ethyl]-4-methylsulfonyl-benzamide,
N-[(1R)-1-cyano-1-methyl-2-(5-chloro-2-{(2,4-dichlorophenoxy}-phenoxy)-ethyl]-4-methylsulfonyl-benzamide,
N-[(1S)-1-cyano-1-methyl-2-(5-chloro-2-{2,4-dichlorophenoxy}-phenoxy)-ethyl]-4-methylsulfonyl-benzamide, The compounds of the present invention may be prepared, for example, by a process characterised in that a compound of formula

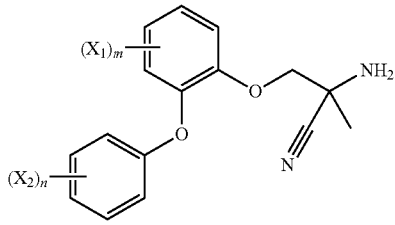

wherein $X_1$, $X_2$, m and n are defined as given for formula I, is reacted with a compound of formula

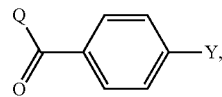

wherein Y is defined as given for formula I and Q is a leaving group, optionally in the presence of a basic catalyst, and if desired, a compound of formula I obtainable according to the method or in another way, respectively in free form or in salt form, is converted info another compound of formula I, a mixture of isomers obtainable according to the method is separated and the desired isomer isolated and/or a free compound of formula I obtainable according to the method is converted into a salt or a salt of a compound of formula I obtainable according to the method is converted into the free compound of formula I or into another salt.

What has been stated above for salts of compounds I also applies analogously to salts of the starting materials listed hereinabove and hereinbelow.

The reaction partners can be reacted with one another as they are, i.e. without the addition of a solvent or diluent, e.g. in the melt. In most cases, however, the addition of an inert solvent or diluent, or a mixture thereof, is of advantage. Examples of such solvents or diluents are: aromatic, aliphatic and alicyclic hydrocarbons and halogenated hydrocarbons, such as benzene, toluene, xylene, mesitylene, tetraline, chlorobenzene, dichlorobenzene, bromobenzene, petroleum ether, hexane, cyclohexane, dichloromethane, trichloromethane, tefrachloromethane, diechloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethylether, dimethoxydiethylether, tetrahydrofuran or dioxane; ketones such as acetone, methyl ethyl ketone or methyl isobutyl ketone; amides such as N,N-dimethylformamide, N,N-diethylformamide, N,N-dimethylacetamide, N-methylpyrrolidone or hexamethylphosphoric acid triamide; nitrites such as acetonitrile or propionitrile; and sulfoxides, such as dimethyl sulfoxide.

Preferred leaving groups Q are halogens, tosylates, mesylates and triflates, most preferably halogens, especially chlorine.

Suitable bases for facilitating the reaction are e.g. alkali metal or alkaline earth metal hydroxides, hydrides, amides, alkanolates, acetates, carbonates, dialkylamides or alkylsilylamides; alkylamines, alkylenediamines, optionally N-alkylated, optionally unsaturated, cycloalkylamines, basic heterocycles, ammonium hydroxides, as well as carbocyclic amines. Those which may be mentioned by way of example are sodium hydroxide, hydride, amide, methanolate, acetate, carbonate, potassium tert-butanolate, hydroxide, carbonate, hydride, lithium diisopropylamide, potassium bis(trimethylsilyl)-amide:, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide, as well as 1,5-diazabicyclo[5.4.0]undec-5-ene (DBU). Preference is given to diisopropylethylamine and 4-(N,N-dimethylamino) pyridine.

The reaction advantageously takes place in a temperature range of ca. 0° C. to ca. 100° C., preferably from ca. 10° C. to ca. 40° C.

Salts of compounds I may be produced in known manner. Acid addition salts of compounds I, for example, are obtainable by treatment with a suitable acid or a suitable ion exchange reagent, and salts with bases are obtainable by treatment with a suitable base or a suitable ion exchange reagent.

Salts of compounds I can be converted into the free compounds I by the usual means, acid addition salts e.g. by treating with a suitable basic composition or with a suitable ion exchange reagent, and salts with bases e.g. by treating with a suitable acid or a suitable ion exchange reagent.

Salts of compounds I can be converted into other salts of compounds I in a known manner; acid addition salts can be converted for example into other acid addition salts, e.g. by treating a salt of an inorganic acid, such as a hydrochloride, with a suitable metal salt, such as a sodium, barium, or silver salt, of an acid, e.g. with silver acetate, in a suitable solvent, in which a resulting inorganic salt, e.g. silver chloride, is insoluble and thus precipitates out from the reaction mixture.

Depending on the method and/or reaction conditions, compounds I with salt-forming characteristics can be obtained in free form or in the form of salts.

Compounds I can also be obtained in the form of their hydrates and/or also can include other solvents, used for example where necessary for the crystallisation of compounds present in solid form.

As mentioned before, the compounds of formula I, Ia or Ib may be optionally present as optical and/or geometric isomers or as a mixture thereof. The invention relates both to the pure isomers and to all possible isomeric mixtures, and is hereinbefore and hereinafter understood as doing so, even if stereochemical details are not specifically mentioned in every case.

Diastereoisomeric mixtures of compounds of formula I, Ia or Ib, which are obtainable by the process or in another way, may be separated in known manner, on the basis of the physical-chemical differences in their components, into the pure diastereoisomers, for example by fractional crystallisation, distillation and/or chromatography.

Splitting of mixtures of enantiomers, that are obtainable accordingly, into the pure isomers, may be achieved by known methods, for example by recrystallisation from an optically active solvent, by chromatography on chiral adsorbents, e.g. high-pressure liquid chromatography (HPLC) on acetyl cellulose, with the assistance of appropriate microorganisms, by cleavage with specific immobilised enzymes, through the formation of inclusion compounds, e.g. using chiral crown ethers, whereby only one enantiomer is complexed. A preferred process for enantiomer separation is disclosed in WO 2006/50887.

According to the invention, apart from separation of corresponding isomer mixtures, generally known methods of diastereoselective or enantioselective synthesis can also be applied to obtain pure diastereoisomers or enantiomers, e.g. by carrying out the method of the invention using educts with correspondingly suitable stereochemistry.

It is advantageous to isolate or synthesise the biologically more active isomer, e.g. enantiomer, provided that the individual components have differing biological efficacy, in general, concerning the compounds of formula I, one of the enantiomers is biologically more active than the other. A preferred embodiment of the invention concerns the (1S)-compounds of the above given formula I', wherein for $X_1$, $X_2$, Y, m and n each the above given meanings and preferences apply.

In the method of the present invention, the starting materials and intermediates used are preferably those that lead to the compounds I described at the beginning as being especially useful.

The starting materials of formula II are known, for example, from WO 2003/104187 or WO 2005/58802 or may be obtained by a process analogous to the ones described therein, The starting materials of the formula III are likewise known, for example, from WO 2003/104187, WO 2005/58802 or WO 2008/96231.

The compounds I according to the invention are notable for their broad activity spectrum and are valuable active ingredients for use in pest control, including in particular the control of endo- and ecto-parasites, especially helminths, in and on warm-blooded animals, especially livestock and domestic animals, whilst being well-tolerated by warm-blooded animals and fish.

In the context of the present invention, ectoparasites are understood to be in particular insects, mites and ticks. These include insects of the order: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera. However, the ectoparasites which may be mentioned in particular are those which trouble humans or animals and carry pathogens, for example flies such as *Musca domestica, Musca vetustissima, Musca autumnalis, Fannia canicularis, Sarcophaga carnaria, Lucilia cuprina, Hypoderma bovis, Hypoderma lineatum, Chrysomyia chloropyga, Dermatobia hominis, Cochliomyia hominivorax, Gasteraphilus intestinalis, Oestrus ovis, Stomoxys calcitrans, Haematobia irritans* and midges (*Nematocera*), such as *Culicidae, Simuliidae, Psychodidae*, but also blood-sucking parasites, for example fleas, such as *Ctenocephalides felis* and *Ctenocephalides canis* (cat and dog fleas), *Xenopsyllae cheopis, Pulex irritans, Dermatophilus penetrans*, lice, such as *Damalina ovis, Pediculus humanis*, biting flies and horseflies (*Tabanidae*), *Haematopota* spp. such as *Haematopota pluvialis, Tabanidae* spp. such as *Tabanus nigrovittatus, Chrysopsinae* spp. such as *Chrysops caecutiens*, tsetse flies, such as species of *Glossinia*, biting insects, particularly cockroaches, such as *Blatella germanica, Blatta orientalis,*

*Periplaneta americana*, mites, such as *Dermanyssus gallinae*, *Sarcoptes scabiei*, *Psoroptes ovis* and *Psorergates* spp. and last but not least ticks. The latter belong to the order Acarina. Known representatives of ticks are, for example, *Boophilus*, *Amblyomma*, *Anocentor*, *Dermacentor*, *Haemaphysalis*, *Hyalomma*, *Ixodes*, *Rhipicentor*, *Margaropus*, *Rhipicephalus*, *Argas*, *Otobius* and *Ornithodoros* and the like, which preferably infest warm-blooded animals including farm animals, such as cattle, pigs, sheep and goats, poultry such as chickens, turkeys and geese, fur-bearing animals such as mink, foxes, chinchillas, rabbits and the like, as well as domestic animals such as cats and dogs, but also humans.

The compounds I according to the invention are also active against all or individual development stages of animal pests showing normal sensitivity, as well as those showing resistance, such as insects and members of the order Acarina. The insecticidal, ovicidal and/or acaricidal effect of the active substances of the invention can manifest itself directly, i.e. killing the pests either immediately or after some time has elapsed, for example when moulting occurs, or by destroying their eggs, or indirectly, e.g. reducing the number of eggs laid and/or the hatching rate, good efficacy corresponding to a pesticidal rate (mortality) of at least 50 to 60%.

Compounds I can also be used against hygiene pests, especially of the order Diptera of the families Sarcophagidae, Anophilidae and Culicidae; the orders Orthoptera, Dictyoptera (e.g. the family Blattidae) and Hymenoptera (e.g. the family Formicidae).

In particular, the compounds are effective against helminths, in which the endoparasitic nematodes and trematodes may be the cause of serious diseases of mammals and poultry, e.g. sheep, pigs, goats, cattle, horses, donkeys, dogs, cats, guinea-pigs and exotic birds. Typical nematodes of this indication are: *Haemonchus*, *Trichostrongylus*, *Ostertagia*, *Nematodirus*, *Cooperia*, *Ascaris*, *Bunostonum*, *Oesophagostonum*, *Charbertia*, *Trichuris*, *Strongylus*, *Trichonema*, *Dictyocaulus*, *Capillaria*, *Heterakis*, *Toxocara*, *Ascaridia*, *Oxyuris*, *Ancylostoma*, *Uncinaria*, *Toxascaris* and *Parascaris*. The trematodes include, in particular, the family of Fasciolideae, especially *Fasciola hepatica*.

It could also be shown surprisingly and unexpectedly that the compounds of formula I have exceptionally high efficacy against nematodes that are resistant to many active substances. This can be demonstrated in vitro by the LDA test and in vivo for example in Mongolian gerbils and sheep. It was shown that amounts of active substance which kill sensitive strains of *Haemonchus contortus* or *Trichostrongylus colubriformis*, are also sufficiently effective at controlling corresponding strains that are resistant to benzimidazoles, levamisol and macrocyclic lactones (for example ivermectin).

Certain pests of the species *Nematodirus*, *Cooperia* and *Oesophagostonum* infest the intestinal tract of the host animal, while others of the species *Haemonchus* and *Ostertagia* are parasitic in the stomach and those of the species *Dictyocaulus* are parasitic in the lung tissue. Parasites of the families Filariidae and Setariidae may be found in the internal cell tissue and in the organs, e.g. the heart, the blood vessels, the lymph vessels and the subcutaneous tissue. A particularly notable parasite is the heartworm of the dog, *Dirofilaria immitis*. The compounds of formula I are highly effective against these parasites. The pests which may be controlled by the compounds of formula I also include those from the class of Cestoda (tapeworms), e.g. the families Mesocestoidae, especially of the genus *Mesocestoides*, in particular *M. lineatus*; Dilepidide, especially *Dipylidium caninum*, *Joyeuxiella* spp., in particular *Joyeuxiella pasquali*, and *Diplopylidium* spp., and Taeniidae, especially *Taenia pisiformis*, *Taenia cervi*, *Taenia ovis*, *Taenia hydatigena*, *Taenia multiceps*, *Taenia taeniaeformis*, *Taenia serialis*, and *Echinococcus* spp., most preferably *Taenia hydatigena*, *Taenia ovis*, *Taenia multiceps*, *Taenia serialis*; *Echinococcus granulosis* and *Echinococcus granulosis* and *Echinococcus multilocularis*, as well as *Multiceps multiceps*.

The compounds of formula I are also suitable for the control of *Coccidiose*, which can appear especially on piglets and chickens. Apart from *Coli* bacteria and *Clostridiae*, *Coccidiae* are one of the most important causes of diarrhoea of unwearied piglets. The most important type in the case of piglets is *Isospora suis*. The piglets become infected with the oocysts (spores) of *Isospora suis* through the mouth. The oocysts migrate into the small intestine, where they penetrate into the small intestinal mucosa. There, they pass through various stages of development. Between the fifth and ninth and the 11th to 14th day after infection, the *Coccidiae* emerge from the intestinal mucosa and are then detectable again in the faeces. This outbreak causes great damage to the intestinal mucosa. The piglets react by exhibiting partly yellowish-pasty to watery diarrhoea. It has a rancid smell. Occasionally, individual piglets vomit. It is customary for the diarrhoea to occur between the eighth and fifteenth day of age.

Most particularly, *Taenia hydatigena*, *T. pisiformis*, *T. ovis*, *T. taeniaeformis*, *Multiceps multiceps*, *Joyeuxiella pasquali*, *Dipylidium caninum*, *Mesocestoides* spp, *Echinococcus granulosis* and *E. multilocularis* are controlled on or in dogs and cats simultaneously with *Dirofilaria immitis*, *Ancylostoma* ssp., *Toxocara* ssp. and/or *Trichuris vulpis*. Equally preferred, *Ctenocephalides felis* and/or *C. canis* are simultaneously controlled with the above-mentioned nematodes and cestodes.

Furthermore, the compounds of formula I are suitable for the control of human pathogenic parasites. Of these, typical representatives that appear in the digestive tract are those of the species *Ancylostoma*, *Necator*, *Ascaris*, *Strongyloides*, *Trichinella*, *Capillaria*, *Trichuris* and *Enterobius*. The compounds of the present invention are also effective against parasites of the species *Wuchereria*, *Brugia*, *Onchocerca* and *Loa* from the family of Filariidae, which appear in the blood, in the tissue and in various organs, and also against *Dracunculus* and parasites of the species *Strongyloidas* and *Trichinella*, which infect the gastrointestinal tract in particular.

In addition, the compounds of formula I are also effective against harmful and pathogenic fungi on humans and animals.

The good pesticidal activity of the compounds of formula I according to the invention corresponds to a mortality rate of at least 50-80% of the pests mentioned. In particular, the compounds of formula I are notable for the exceptionally long duration of efficacy. The compounds of formula I are preferably employed in unmodified form or preferably together with the adjuvants conventionally used in the art of formulation and may therefore be processed in a known manner to give, for example, emulsifiable concentrates, directly dilutable solutions, dilute emulsions, soluble powders, granules or microencapsulations in polymeric substances. As with the compositions, the methods of application are selected in accordance with the intended objectives and the prevailing circumstances.

The formulation, i.e. the agents, preparations or compositions containing the active ingredient of formula I, or combinations of these active ingredients with other active ingredients, and optionally a solid or liquid adjuvant, are produced in a manner known per se, for example by intimately mixing and/or grinding the active ingredients with spreading compositions, for example with solvents, solid carriers, and optionally surface-active compounds (surfactants).

The solvents in question may be: alcohols, such as ethanol, propanol or butanol, and glycols and their ethers and esters, such as propylene glycol, dipropylene glycol ether, ethylene glycol, ethylene glycol monomethyl or -ethyl ether, ketones, such as cyclohexanone, isophorone or diacetanol alcohol, strong polar solvents, such as N-methyl-2-pyrrolidone, dimethyl sulfoxide or dimethylformamide, or water, vegetable oils, such as rape, castor, coconut, or soybean oil, and also, if appropriate, silicone oils.

Preferred application forms for usage on warm-blooded animals in the control of helminths include solutions, emulsions, suspensions (drenches), food additives, powders, tablets including effervescent tablets, boli, capsules, micro-capsules and pour-on formulations, whereby the physiological compatibility of the formulation excipients must be taken into consideration.

The binders for tablets and boli may be chemically modified polymeric natural substances that are soluble in water or in alcohol, such as starch, cellulose or protein derivatives (e.g. methyl cellulose, carboxymethyl cellulose, ethylhydroxyethyl cellulose, proteins such as zein, gelatin and the like), as well as synthetic polymers, such as polyvinyl alcohol, polyvinyl pyrrolidone etc. The tablets also contain fillers (e.g. starch, microcrystalline cellulose, sugar, lactose etc.), glidants and disintegrants.

If the anthelminthics are present in the form of feed concentrates, then the carriers used are e.g. performance feeds, feed grain or protein concentrates. Such feed concentrates or compositions may contain, apart from the active ingredients, also additives, vitamins, antibiotics, chemotherapeutics or other pesticides, primarily bacteriostats, fungistats, coccidiostats, or even hormone preparations, substances having anabolic action or substances which promote growth, which affect the quality of meat of animals for slaughter or which are beneficial to the organism in another way. If the compositions or the active ingredients of formula I contained therein are added directly to feed or to the drinking troughs, then the formulated feed or drink contains the active ingredients preferably in a concentration of ca. 0.0005 to 0.02% by weight (5-200 ppm).

The compounds of formula I according to the invention may be used alone or in combination with other biocides. They may be combined with pesticides having the same sphere of activity e.g. to increase activity, or with substances having another sphere of activity e.g. to broaden the range of activity. It can also be sensible to add so-called repellents, if the range of activity is to be extended to endoparasites, e.g. wormers, the compounds of formula I are suitably combined with substances having endoparasitic properties. Of course, they can also be used in combination with antibacterial compositions. Since the compounds of formula I are adulticides, i.e. since they are effective in particular against the adult stages of the target parasites, the addition of pesticides which instead attack the juvenile stages of the parasites may be very advantageous. In this way, the greatest part of those parasites that produce great economic damage will be covered. Moreover, this action will contribute substantially to avoiding the formation of resistance. Many combinations may also lead to synergistic effects, i.e. the total amount of active ingredient can be reduced, which is desirable from an ecological point of view. Preferred groups of combination partners and especially preferred combination partners are named in the following, whereby combinations may contain one or more of these partners in addition to a compound of formula I.

Suitable partners in the mixture may be biocides, e.g. the insecticides and acaricides with a varying mechanism of activity, which are known to the person skilled in the art, e.g. chitin synthesis inhibitors, growth regulators; active ingredients which act as juvenile hormones; active ingredients which act as adulticides; broad-band insecticides, broad-band acaricides and nematicides; and also the well known anthelminthics, insect- and/or acarid-deterring substances, repellents, detachers or synergists.

Non-limitative examples of suitable insecticides and acaricides are mentioned in WO 2009/071500, compounds Nos. 1-284 on pages 18-21. Non-limitative examples of suitable anthelminthics are mentioned in WO 2009/071500, compounds (A1)-(A31) on page 21. Non-limitative examples of suitable repellents and detachers are mentioned in WO 2009/071500, compounds (R1)-(R3) on page 21 and 22. Non-limitative examples of suitable synergists are mentioned in WO 2009/071500, compounds (S1)-(S3) on page 22.

Accordingly, a further essential aspect of the present invention relates to combination preparations for the control of parasites on warm-blooded animals, characterised in that they contain, in addition to a compound of formula I, at least one further active ingredient having the same or different sphere of activity and at least one physiologically acceptable carrier. The present invention is not restricted to two-fold combinations.

In one embodiment of the invention, the compound of formula I is used in combination with one or more further anthelmintic agents. Such a combination may reduce further the likelihood of resistance developing. Suitable further anthelmintic agents include:
(i) a macrocyclic lactone, for example ivermectin, avermectin, abamectin, emamectin, eprinomectin, doratectin, selamectin, moxidectin, nemadectin, milbemycin or a derivative thereof, for example milbemycin oxim;
(ii) a benzimidazole, for example albendazole, cambendazole, fenbendazole, flubendazole, mebendazole, oxfendazole, oxibendazole or parbendazole;
(ill) an imidazothiazole or tetrahydropyrimidine, for example tetramisole, levamisole, pyrantel, pamoate, oxantel or morantel;
(iv) a cyclic depsipeptide, for example emodepside; and
(v) derivatives and analogues of the paraherquamide/marcfortine class, in particular paraherquamide A or derquantel.

In another embodiment of the invention, the compound of formula I is used in combination with one or more ectoparasiticidal compound. Suitable ectoparasiticidal compounds include:
(i) aryl pyrazoles, for example fipronil, pyriprole or pyrafluprole;
(ii) pyrethroids;
(iii) insect growth regulators, for example lufenuron;
(iv) spinosyns, for example spinosad, spinetoram;
(v) neonicotinoids, for example imidacloprid, dinotefuran; and
(vi) various other insecticides, for example metaflumizone, flubendiamide, indoxacarb.

In case of mixtures of two or more active ingredients, the different active ingredients may be administered simultaneously, for example in a single dosage unit such as a single pour-on solution; sequentially or separately. Combinations of different active ingredients also may be presented in kit form.

As a rule, the anthelminthic compositions according to the invention contain 0.1 to 99% by weight, especially 0.1 to 95% by weight of active ingredient of formula I or mixtures thereof, 99.9 to 1% by weight, especially 99.8 to 5% by weight of a solid or liquid admixture, including 0 to 25% by weight, especially 0.1 to 25% by weight of a surfactant. Application of the compositions according to the invention to the animals to be treated may take place topically, perorally, parenterally or subcutaneously, the composition being present, for example, in the form of a solution, emulsion, suspension, (drenche), powder, tablet, boli, capsule or pour-on- or spot-on formulation. Most preferably, the compositions of the present invention are applied orally or as an injectable, the compositions being present in the form of a solution, emulsion suspension or suspoemulsion.

The pour-on or spot-on method consists in applying the compound of formula I to a specific location of the skin or coat, advantageously to the neck or backbone of the animal. This takes place e.g. by applying a swab or spray of the pour-on or spot-on formulation to a relatively small area of the coat, from where the active substance is dispersed almost automatically over wide areas of the fur owing to the spreading nature of the components in the formulation and assisted by the animal's movements.

Examples of suitable carriers within the liquid formulations are e.g. oily solutions; alcoholic and isopropanolic solutions such as solutions of 2-octyldodecanol or oleyl alcohol; solutions in esters of monocarboxylic acids, such as isopropyl myristate, isopropyl palmitate, lauric acid oxalate, oleic acid oleyl ester, oleic acid decyl ester, hexyl laurate, oleyl oleate, decyl oleate, capric acid esters of saturated fat alcohols of chain length $C_{12}$-$C_{18}$; solutions of esters of dicarboxylic acids, such as dibutyl phthalate, diisopropyl isophthalate, adipic acid diisopropyl ester, di-n-butyl adipate or also solutions of esters of aliphatic acids, e.g. glycols. It may be advantageous for a dispersing agent to be additionally present, such as one known from the pharmaceutical or cosmetic industry. Examples are 2-pyrrolidone, 2-(N-alkyl)pyrrolidone, acetone, polyethylene glycol and the ethers and esters thereof, propylene glycol or synthetic triglycerides. In case of oily solutions said solutions may include e.g. vegetable oils such as olive oil, groundnut oil, sesame oil, pine oil, linseed oil or castor oil. The vegetable oils may also be present in epoxidised form. Paraffins and silicone oils may also be used.

Whereas it is preferred to formulate commercial products as concentrates, the end user will normally use dilute formulations.

Such compositions may also contain further additives, such as stabilisers, anti-foaming agents, viscosity regulators, binding agents or tackifiers, as well as other active ingredients, in order to achieve special effects.

Anthelminthic compositions of this type, which are used by the end user, similarly form a constituent of the present invention.

In each of the processes according to the invention for pest control or in each of the pest control compositions according to the invention, the active ingredients of formula I can be used in all of their steric configurations or in mixtures thereof.

The invention also includes a method of prophylactically protecting warm-blooded animals, especially productive livestock, domestic animals and pets, against parasitic helminths, which is characterised in that the active ingredients of the formula or the active ingredient formulations prepared therefrom are administered to the animals as an additive to the feed, or to the drinks or also in solid or liquid form, orally or by injection or parenterally. The invention also includes the compounds of formula I according to the invention for usage in one of the said processes.

The compounds and compositions of the present invention are especially advantageous for use on herd animals such as cattle, horses, sheep, goat or pigs, in particular cattle, goat and sheep; of course they also can be used for all other animals, including individual domestic animals or pets.

The following Examples illustrate the invention further.

PREPARATION EXAMPLES

Example 1

N-[1-cyano-1-methyl-2-(5-cyano-2-{2-chloro-4-trifluoromethoxy-phenoxy}-phenoxy)-ethyl]-4-pentafluorothio-benzamide

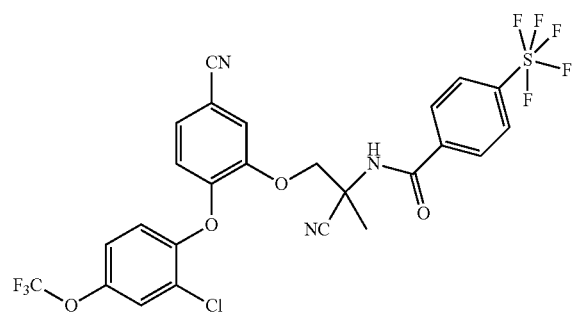

a) 12.8 g of 4-fluro-3-methoxybenzonitrile are dissolved in 100 mL of dichloromethane. 250 mL of a 1M solution of borontribromide in dichloromethane are slowly added over 50 min. The reaction mixture is then stirred for 5 days at room temperature. After cooling to 0° C. water is added carefully until no reaction is observed anymore. The reaction mixture is washed with water, a saturated aqueous solution of sodium bicarbonate and with brine. The organic phase is dried with magnesium sulfate and evaporated under vacuum. The residue is recrystallized from ether/hexanes to yield 4-fluoro-3-hydroxybenzonitrile.

b) 8.9 g of 4-fluoro-3-hydroxybenzonitrile, 12.0 g of chloroacetone, 11.2 g of potassium carbonate and 0.60 g of potassium iodide are dissolved in 150 mL of acetone and boiled under reflux for 5 hours. After cooling the precipitate is filtered, concentrated by evaporation, redissolved in ethylacetate and washed with 1N aqueous solution of sodium bicarbonate, water, 1N aqueous solution of hydrogen chloride and finally with brine. The organic phase is dried with magnesium sulfate and evaporated under vacuum. The residue is crystallized from ether to yield 4-fluoro-3-(2-oxo-propoxy)-benzonitrile.

c) 10.3 g of 4-fluoro-3-(2-oxo-propoxy)-benzonitrile, 6.6 g of ethyleneglycol and 2.3 g of p-toluenesulfonic acid are dissolved in 150 mL of toluene in a Dean-Stark apparatus. The solution is refluxed for 2 hours and then allowed to cool to room temperature. The reaction mixture is diluted with ethyl acetate and washed with water, a 1N aqueous solution of sodium hydroxide, water and brine. The organic phase is dried with magnesium sulfate and evaporated under vacuum. The residue is crystallized from hexanes to yield 4-fluoro-3-(2-methyl-[1,3]dioxolan-2-ylmethoxy)-benzonitrile.

d) 6.6 g of 4-fluoro-3-(2-methyl-[1,3]dioxolan-2-ylmethoxy)-benzonitrile, 7.2 g of 2-chlor-4-(trifluormethoxy)phenol and 11.8 g of cesium carbonate are dissolved in 150 mL of dimethylformamide and stirred at 120° C. for 20 hours. After cooling the solution is diluted with diethyl ether, washed with water, a 1N aqueous solution of sodium hydroxide, water and finally with brine. The organic phase is dried with magnesium sulfate and evaporated under vacuum. The residue is purified by column chromatography (ethyl acetate/hexanes) to yield 4-(2-chloro-4-trifluoromethoxy-phenoxy)-3-(2-methyl-[1,3]dioxolan-2-ylmethoxy)-benzonitrile.

e) 7.4 g of 4-(2-chloro-4-trifluoromethoxy-phenoxy)-3-(2-methyl-[1,3]dioxolan-2-ylmethoxy)-benzonitrile and 20 mL of a 2N aqueous solution of hydrogen chloride are dissolved in 40 mL of acetone. The solution is stirred at 60° C. for 20 hours and concentrated under vacuum. The residue is dissolved in ethyl acetate and washed with water, a saturated aqueous solution of sodium bicarbonate and with brine. The organic phase is dried with magnesium sulfate and evaporated under vacuum. The residue is recrystallized from ether/hexanes to yield 4-(2-chloro-4-trifluoromethoxy-phenoxy)-3-(2-oxo-propoxy)-benzonitrile.

f) 5.8 g of 4-(2-chloro-4-trifluoromethoxy-phenoxy)-3-(2-oxo-propoxy)-benzonitrile, 0.9 g of sodium cyanide and 1 g of ammonium chloride are suspended in 40 mL of ethanol, 20 mL of a 25% aqueous solution of ammonia are then added. The solution is stirred at room temperature for 16 hours and concentrated under vacuum. The residue is dissolved in ethyl acetate and washed with water and brine. The organic phase is dried with magnesium sulfate and evaporated under vacuum. The residue is recrystallized from ether/hexanes to yield 3-(2-amino-2-cyano-2-methyl-ethoxy)-4-(2-chloro-4-trifluoromethoxy-phenoxy)-benzonitrile.

g) 150 mg of 4-pentafluorothio-benzoic acid are dissolved in 1 mL of thionyl chloride and stirred under reflux for 1 hour. The reaction mixture is concentrated under vacuum and dissolved in 1.5 mL of dichloromethane. This solution is added to a solution of 250 mg of 3-(2-amino-2-cyano-2-methyl-ethoxy)-4-(2-chloro-4-trifluoromethoxy-phenoxy)-benzonitrile and 0.23 ml of N,N-diisopropylamine in 3.5 mL of dichloromethane at 0° C. The reaction mixture is stirred at room temperature for 20 hours and washed with water. The organic phase is dried with magnesium sulfate and evaporated under vacuum. The residue is purified by column chromatography (ethyl acetate/hexanes/methanol) and recrystallized from chloroform/heptane to yield the title compound as a colorless solid.

The compounds named in Table 1 below may also be prepared analogously to the above-described method. The values of the melting points are given in ° C.

TABLE 1

| No. | Y | $(X_1)_m$ | $(X_2)_n$ | phys. data |
|---|---|---|---|---|
| 1.1 | $SF_5$ | 5-Cl | 2,4-$Cl_2$ | m.p. 158-160° C. |
| 1.2 | $SF_5$ | 5-CN | 2,4-$Cl_2$ | m.p. 169-170° C. |
| 1.3 | $SF_5$ | 5-CN | 2-Br—4-F | m.p. 147-149° C. |
| 1.4 | $SF_5$ | 5-CN | 2-Cl—4-F | m.p. 154-156° C. |
| 1.5 | $SF_5$ | 5-CN | 2-Cl—4-$OCF_3$ | m.p. 173-174° C. |
| 1.6 | $SCF_3$ | 5-Cl | 2,4-$Cl_2$ | m.p. 145-146° C. |
| 1.7 | $SCF_3$ | 5-Cl | 2-Br, 3,5-$F_2$ | paste |
| 1.8 | $SCF_3$ | 4-Cl | 2,4-$Cl_2$ | m.p. 152-153° C. |
| 1.9 | $SCF_3$ | 4-Br | 2,4-$Cl_2$ | m.p. 145-148° C. |
| 1.10 | $S(O_2)CH_3$ | 5-Cl | 2,4-$Cl_2$ | m.p. 123-124° C. |

BIOLOGICAL EXAMPLES

1. Activity in vitro Against *Trichostrongylus colubriformis* and *Haemonchus contortus*

Freshly harvested and cleaned nematode eggs are used to seed a suitably formatted 96-well plate containing the test substances to be evaluated for antiparasitic activity. Each compound is tested by serial dilution in order to determine its MED. The test compounds are embedded in an agar-based nutritive medium allowing the full development of eggs through to $3^{rd}$ instar larvae. The plates are incubated for 6 days at 25° C. and 60% relative humidity (RH). Egg-hatching and ensuing larval development are recorded to identify a possible nematodicidal activity.

Efficacy is expressed in percent reduced egg hatch, reduced development of L3, or paralysis & death of larvae of all stages.

The following compounds from Table 1 show more than 90% ($EC_{90}$) efficacy against both worms at 0.1 ppm: 1.1-1.7 and 1.10.

2. In-vivo Test on *Trichostrongylus colubriformis* and *Haemonchus contortus* on Mongolian Gerbils (*Meriones unguiculatus*) Using Peroral Application Six to eight week old Mongolian gerbils are infected through a stomach tube with ca. 2000 third instar larvae each of *T. colubriformis* and *H. contortus*. 6 days after infection, the gerbils are treated by peroral application with the test compounds, dissolved in a mixture of 2 parts DMSO and 1 part polyethylene glycol (PEG 400). On day 9 (3 days after treatment), when most of the *H. contortus* that are still present are late 4th instar larvae and most of the *T. colubriformis* are immature adults, the gerbils are killed in order to count the worms. The efficacy is calculated as the % reduction of the number of worms in each gerbil, compared with the geometric average of number of worms from 6 infected and untreated gerbils.

In this test, a vast reduction in nematode infestation is achieved with compounds of formula I, in particular, compound 1.1 from Table 1 shows more than 95% efficacy against both worms at a dose of 1 mg/kg, compounds 1.2, 1.3 and 1.5 from Table 1 show more than 95% efficacy against both worms at a dose of 0.32 mg/kg.

2a. In-vivo Test on *Trichostronglyus colubriformis* and *Haemonchus contortus* in Mongolian Gerbils The above described in-vivo test on *Trichostrongylus colubriformis* (Tc) and *Haemonchus contortus* (Hc) was repeated with compounds 1.2, 1.3 and 1.5 from Table 1 and with the compounds of Examples 1a and 3a on pages 22-25 of WO 2008/96231. The compounds showed the following efficacies, each at 0.32 mg/kg;

| Compound | Efficacy against Tc [%] | Efficacy against Hc [%] |
| --- | --- | --- |
| Example 1.2 | 100 | 98 |
| Example 1.3 | 98 | 100 |
| Example 1.5 | 99 | 100 |
| Example 1a WO 2008/96231 | 33 | 85 |
| Example 3a WO 2008/96231 | 23 | 40 |

To examine the insecticidal and/or acaricidal activity of the compounds of formula I on animals and plants, the following test methods may be used.

3. Activity on $L_1$ Larvae of *Lucilia sericata*

1 ml of an aqueous suspension of the active substance to be tested is admixed with 3 ml of a special larvae growth medium at ca. 50° C., so that a homogenate of either 250 or 125 ppm of active ingredient content is obtained. Ca. 30 *Lucilia* larvae ($L_1$) are used in each test tube sample. After 4 days, the mortality rate is determined.

4. Acaricidal Activity on *Boophilus microplus* (Biarra Strain)

A piece of sticky tape is attached horizontally to a PVC sheet, so that 10 fully engorged female ticks of *Boophilus microplus* (Biarra strain) can be adhered thereto by their backs, side by side, in a row. Using an injection needle, 1 μl of a liquid is injected into each tick. The liquid is a 1:1 mixture of polyethylene glycol and acetone and it contains, dissolved therein, a certain amount of active ingredient chosen from 1, 0.1 or 0.01 μg per tick. Control animals are given an injection without active ingredient. After treatment, the animals are kept under normal conditions in an insectarium at ca. 28° C. and at 80% relative humidity until oviposition takes place and the larvae have hatched from the eggs of the control animals. The activity of a tested substance is determined by $IR_{90}$, i.e. an evaluation is made of the dosage of active ingredient at which 9 out of 10 female ticks (=90%) lay eggs that are infertile even after 30 days.

5. In vitro Efficacy on Engorged Female *Boophilus microplus* (BIARRA)

4×10 engorged female ticks of the OP-resistant BIARRA strain are adhered to a sticky strip and covered for 1 hour with a cotton-wool ball soaked in an emulsion or suspension of the test compound in concentrations of 500, 125, 31 and 8 ppm respectively. Evaluation takes place 28 days later based on mortality, oviposition and hatched larvae.

An indication of the activity of the test compounds is shown by the number of females that
 die quickly before laying eggs,
 survive for some time without laying eggs,
 lay eggs in which no embryos are formed,
 lay eggs in which embryos form, from which no larvae hatch, and
 lay eggs in which embryos form, from which larvae normally hatch within 26 to 27 days.

6. In vitro Efficacy on Nymphs of *Amblyomma hebraeum*

About 5 fasting nymphs are placed in a polystyrene test tube containing 2 ml of the test compound in solution, suspension or emulsion.

After immersion for 10 minutes, and shaking for 2×10 seconds on a vortex mixer, the test tubes are blocked up with a tight wad of cotton wool and rotated. As soon as all the liquid has been soaked up by the cotton wool ball, it is pushed half-way into the test tube which is still being rotated, so that most of the liquid is squeezed out of the cotton-wool ball and flows into a Petri dish below.

The test tubes are then kept at room temperature in a room with daylight until evaluated. After 14 days, the test tubes are immersed in a beaker of boiling water. If the ticks begin to move in reaction to the heat, the test substance is inactive at the tested concentration, otherwise the ticks are regarded as dead and the test substances regarded as active at the tested concentration. All substances are tested in a concentration range of 0.1 to 100 ppm.

7. Activity Against *Dermanyssus gallinae*

2 to 3 ml of a solution containing 10 ppm active ingredient, and ca. 200 mites (*Dermanyssus gallinae*) at different stages of development are added to a glass container which is open at the top. Then the container is closed with a wad of cotton wool, shaken for 10 minutes until the mites are completely wet, and then inverted briefly so that the remaining test solution can be absorbed by the cotton wool. After 3 days, the mortality of the mites is determined by counting the dead individuals and indicated as a percentage.

8. Activity Against *Musca domestica*

A sugar cube is treated with a solution of the test substance in such a way that the concentration of test substance in the sugar, after drying over night, is 250 ppm. The cube treated in this way is placed on an aluminium dish with wet cotton wool and 10 adult *Musca domestica* of an OP-resistant strain, covered with a beaker and incubated at 25° C. The mortality rate is determined after 24 hours.

What we claim is:

1. A compound of formula

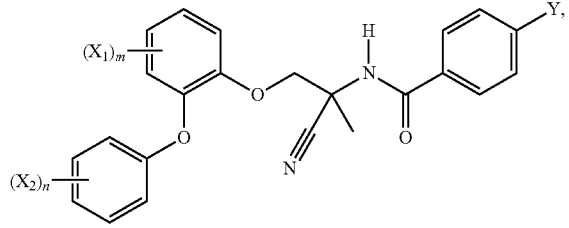

wherein
X$_1$ signifies cyano or halogen, whereby if m is greater than 1, the meanings of X$_1$ may be identical or different;
X$_2$ signifies halogen, cyano, C$_1$-C$_6$-alkyl, C$_1$-C$_6$-haloalkyl, C$_1$-C$_6$-alkoxy, C$_1$-C$_6$-haloalkoxy, C$_1$-C$_6$-haloalkylthio or SF$_5$,
whereby if n is greater than 1, the meanings of X$_2$ may be identical or different;
Y is C$_1$-C$_2$-haloalkyl, SR, S(O)R, S(O$_2$)R or SF$_5$,
R is C$_1$-C$_6$-alkyl or C$_1$-C$_6$-haloalkyl,
m signifies 1, 2, 3 or 4; and
n is 1, 2, 3, 4 or 5;
subject to the proviso, that Y is SF$_5$ if X$_1$ is cyano.

2. A compound of formula I, according to claim 1, wherein Y is SF$_5$.

3. A compound of formula I according to claim 2, wherein m is 1 and X$_1$ is cyano.

4. A compound of formula I, according to claim 1, wherein Y is C$_1$-C$_2$-haloalkyl, SR, S(O)R or S(O$_2$)R, and each X$_1$ independently of the other is halogen.

5. A compound of formula I according to claim 1, wherein R is C$_1$-C$_2$-alkyl or C$_1$-C$_2$-haloalkyl.

6. A compound of formula I according to claim 1, wherein m is 1.

7. A compound of formula I according to claim 1, wherein X$_2$ is halogen, CF$_3$ or OCF$_3$.

8. A compound of formula I according to claim 1, wherein n is 2 or 3.

9. A compound according to claim 1 of formula

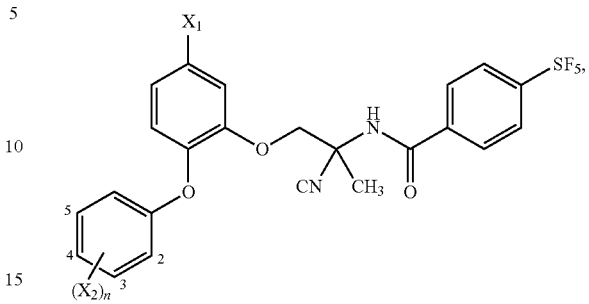

wherein X$_1$ is cyano or halogen, n is 2 or 3, and each X$_2$ independently of the other is halogen, CF$_3$ or OCF$_3$.

10. A compound according to claim 1 of formula

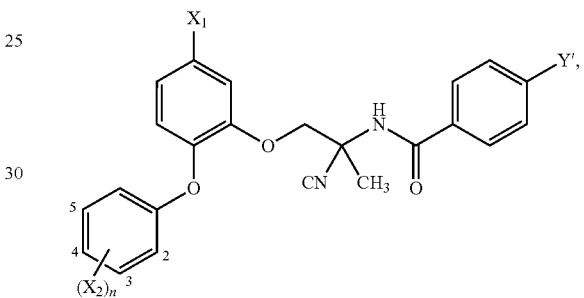

wherein Y' is CF$_3$, SCF$_3$, S(O$_2$)CF$_3$ or S(O$_2$)CH$_3$, X$_1$ is halogen, n is 2 or 3, and each X$_2$ is independently halogen, CF$_3$ or OCF$_3$.

11. Composition for the control of parasites, which contains as an active ingredient at least one compound of formula I according to claim 1, in addition to carriers and/or dispersants.

12. Method of controlling parasites, comprising applying an effective amount of at least one compound of formula I according to claim 1 to an animal.

13. A compound of formula I according to claim 5, wherein R is methyl, ethyl or CF$_3$.

14. A compound of formula I according to claim 7, wherein X$_2$ is bromine, chlorine, fluorine or OCF$_3$.

15. A compound of formula I according to claim 8, wherein n is 2.

* * * * *